(12) United States Patent
Hamtini

(10) Patent No.: US 6,911,196 B2
(45) Date of Patent: Jun. 28, 2005

(54) TOPICAL MEDICAMENT FOR TREATING NAPPY RASH

(76) Inventor: Samir I. Hamtini, 20-20 Menahan St., Ridgewood, NY (US) 11385

( * ) Notice: Subject to any disclaimer, the term of this patent is extended or adjusted under 35 U.S.C. 154(b) by 380 days.

(21) Appl. No.: 10/209,160

(22) Filed: Jul. 31, 2002

(65) Prior Publication Data

US 2004/0022863 A1 Feb. 5, 2004

(51) Int. Cl.$^7$ .................. A61K 31/74; A61K 33/22; A61K 31/19; A01N 37/10
(52) U.S. Cl. .................. 424/78.08; 424/659; 514/570
(58) Field of Search .............. 424/78.07, 659; 514/570

(56) References Cited

U.S. PATENT DOCUMENTS 3,964,486 A * 6/1976 Blaney ................. 604/360

* cited by examiner

Primary Examiner—Alton Pryor

(57) ABSTRACT

A composition and method of treating nappy rash utilizes a combination of Salicylic Acid (0.720/100 g), Boric Acid (5 g/100 g), Tannic Acid (0.575 g/100 g), Zinc oxide (5 g/100 g), Calamine (1.5 g/100 g), and Lanolin (2 g/100 g). Many oils have been also introduced into the composition and method including Olive oil (20.00 ml), Castor oil (10.00 ml), and Cod Liver oil (10.00 ml). Cetrimide (0.0075 g/100 g) and White Petroleum Q.S.100 g are added to the composition and method.

1 Claim, No Drawings

TOPICAL MEDICAMENT FOR TREATING NAPPY RASH

BACKGROUND OF THE INVENTION

The presented invention relates generally to the field of treating a skin condition known as Nappy (Diaper) Rash. The presented invention relates to topically applied medicinal composition and more particularly to such composition active topical medicinal ingredients including Salicylic acid, Boric acid, Tannic acid, Zinc oxide, Calamine, Cetrimide, White petroleum, and rich oil formula; Olive oil, castor oil, and Cod liver oil. The presented invention finds utility in topically treating other certain types of dermatological disorders such as Bedsores, Skin ulcers, Athlete's foot (Tines Pedis), bruises, burns, abrasions, cuts, Eczema, Psoriasis and others. The composition also provides longlasting relief from such symptoms when applied topically to areas of the patient's skin that are affected.

SUMMARY OF THE INVENTION

The invention provides a unique and complete treatment of nappy rash that is nor provided in other available treatment. The invention works as a healer of damaged skin as it seals the affected area from other damaging elements. The fact that makes it most effective against nappy rash and other similar dermatological disorders is its anti-septic nature combined with its sealing ability, the introduction of both Tannic and Salicylic Acids into the formula makes it a one of a kind formula since it is the first formula to use these acids in the treatment of nappy rash.

DETAILED DESCRIPTION OF THE INVENTION

The applicants has established that when these agents may be combined in accordance with invention as in an ointment for example had not degraded and remained stable after prolonged storage. The presented invention is concerned with composition for treating Nappy rash and particularly to composition containing Salicylic acid, Boric acid, Tannic acid, Zinc oxide, Calamine, and Cetrimide in combination with Lanolin, White Petroleum and the oils; Olive oil, Castor oil, and Cod liver oil for treating nappy rash. These ingredients form a unique and comprehensive formula to provide perfect and complete treatment of several dermatological disorders. It combines the Bacteriostatic, fungicided action of Salicylic acid together with its anti-inflammatory and good antiseptic effects. This action is considerably enhanced by the presence of Boric acid with its broad-spectrum Bacteriostatic, fungestatic properties. The introduction of Tannic acid is of particular value due to its strong astringent action which helps to relief pain quickly and contributes to the overall healing effect. Olive oil, Castor oil, and Cod liver oil have been added to the formula with Lanolin and White Petroleum to create great emollient, soothing and calming effects through forming an occlusive layer on the skin, making the invention a successful water-repellent barrier thus prevent loss of normal skin moisture content on one hand and protect it from outside water on the other. Moreover, this layer reduces friction of skin in the interregional areas and reduces contact with clothes leading to additional protection and disinfecting of skin. The optimally composed formula with its emollient properties, also contributes to the curative effect. Zinc oxide and Calamine exert astringent and protective effects, which have great advantage. Cetrimide; being Quaternary Ammonium compound, with its specific antiseptic properties will leave the skin fresh, clean, with a nice odor to it. These ingredients in the composition are stable and well tolerated. Because of their properties, compositions, according to the invention they are suitable for treatment of several dermatological disorders such as nappy rash. The primary objective of the present invention is to provide composition and method for treating nappy rash by utilizing topical anti-infective agents together with emollients and oil. Another objective of the present invention is a pharmaceutical composition, which reduces related symptoms of nappy rash such as aggravated skin, redness, itching, wounds, abrasions, irritation, and offensive odor. The treatment—which the present invention provide— is both an immediate relief of the pain and a long lasting healing effect. Another objective of the presented invention is to provide effective treatment of a wide variety of fungal and bacterial skin infection particularly those occurring in the interregional areas (thighs and underarms) since those areas are exposed to excessive sweating which rarely vaporizes. It acts as emollient, antiseptic, and as an astringent of wounds and lesions occurring in those areas. It is an objective of the presented invention to provide topically applied pharmaceutical composition containing several topical antibacterial, anti fungal, and anti septic agents together with the oils and the white petroleum suitable for prophylaxis and treatment of various ailments and superficial abrasion conditions of the skin such as bedsores, dryness, skin ulcers, minor abrasions, eczema, psoriasis, and vitamin-A deficiency and as adjuvant therapy in cases of Athlete's foot due to the anti fungal properties of Salicylic acid and Boric acid. The other object is to provide topical compositions of the type described for the treatment of nappy rash and more particularly severe forms which the compositions is more effective as a remedy than compositions presently known and used in the art. Final objective is a formula that provides topical therapy with no or little side effects and which doesn't have the risk of bearing toxic residues and is economical in cost to both manufacturer and patient. According to the invention, it has been further found that many patients with severe inflamed cases, referring to even long term treatment with a variety of conventional remedies experience significant importance in their conditions when treated within two days many times daily using the combination of the invention. The foregoing and other objects, advantages and characterizing features will become apparent from the following descriptions of certain illustrative embodiments of the invention. The features which are considered characteristic for the invention are set forth in the appended claims.

The invention employs a composition for treating diaper rash comprising a combination of 0.720 g/100 g Salicylic acid, 5 g/100 g boric acid, 0.575 g/100 g tannic acid, 5 g/100 g zinc oxide, 1.5 g/100 g calamine, 2 g/100 g lanolin, 20 ml olive oil, 10 ml castor oil, 10.00 ml cod liver oil, 0.0075 g/100 g cetrimide and white petroleum Q.S. 100 g.

I claim:

1. A Topical diaper rash composition that consist of
   a) Boric Acid in a concentration of 5 g/100 g,
   b) Zinc oxide in a concentration of 5 g/100 g,
   c) Calamine in a concentration of 1.5 g/100 g,
   d) Cetrimide in a concentration of 0.0075 g/100 g,
   e) Olive Oil of 20.00 ml,
   f) Castor Oil of 10.00 ml,
   g) Cod liver Oil of 20.00 ml,
   h) White Petroleum base Q.S. 100 g,
   i) Salicylic Acid in a concentration of 0.720 g/100 g,
   j) Tannic Acid in a concentration of 0.575 g/100 g.

* * * * *